United States Patent [19]

Mochizuki et al.

[11] Patent Number: 4,675,347
[45] Date of Patent: Jun. 23, 1987

[54] ANTIMICROBIAL LATEX COMPOSITION

[75] Inventors: Masatsugu Mochizuki, Shiga; Yoshihiro Umemura, Kyoto; Izumi Sakammoto, Kyoto; Kunihiko Takagi, Kyoto, all of Japan

[73] Assignee: Unitika Ltd., Amagasaki, Japan

[21] Appl. No.: 664,177

[22] Filed: Oct. 24, 1984

[30] Foreign Application Priority Data

Oct. 29, 1983 [JP] Japan .............................. 58-203492
Oct. 29, 1983 [JP] Japan .............................. 58-203493

[51] Int. Cl.$^4$ ..................... A61M 25/00; B44D 1/22
[52] U.S. Cl. ................... 523/122; 106/15.05; 106/16
[58] Field of Search ............... 106/15.05, 16; 523/122

[56] References Cited

U.S. PATENT DOCUMENTS 3,325,436  6/1967  Prindle et al. ..................... 523/122
3,695,921 10/1972  Shepherd et al. ................ 427/412.4

Primary Examiner—John Kight
Assistant Examiner—M. L. Moore
Attorney, Agent, or Firm—Sughrue, Mion, Zinn, Macpeak, and Seas

[57] ABSTRACT

An antimicrobial latex composition is disclosed. The antimicrobial latex composition comprises (1) at least one cationic latex component selected from a cationic natural rubber latex and a cationic synthetic polymer latex and (2) a cationic antimicrobial agent incorporated in said cationic latex (1). The resulting composition is antimicrobial latex compositions suitable for use in the manufacture of medical devices and appliances, sanitary products, equipment and furnishings for use in food manufacture and processing, and so forth, in particular antimicrobial latex compositions retaining good stability over a long period of storage.

14 Claims, No Drawings

4,675,347

ANTIMICROBIAL LATEX COMPOSITION

FIELD OF THE INVENTION

This invention relates to antimicrobial latex compositions. More particularly, it relates to antimicrobial latex compositions suitable for use in manufacturing medical equipment and appliances and other shaped articles having a persistent antimicrobial activity.

This invention also relates to shaped articles made of the antimicrobial latex compositions and capable of allowing a slow release of an antimicrobial agent therefrom and to a method of manufacturing such articles.

BACKGROUND OF THE INVENTION

Catheterization in human patients is often required in treating a variety of diseases. However, catheterization provides a direct passage from the outside into the patient's body and therefore the catheterized person may be exposed to risks of bacterial or fungal infection and, further, of severe septicemia. For instance, in patients with bone marrow lesions or cerebrovascular disorders or postoperative patients, who suffer from dysuria or urinary incontinence, urethral catheterization is widely used for the purpose of securing smooth urethral passage, maintaining or improving kidney functions, or preventing urine leakage. However, it is known that, since urethral catheters are left in the urinary tract for a prolonged period of time, bacterial invasion via the inside or outside of such catheters occurs and causes, in high incidences, uretheritis, cystitis and pyelonephritis, among others. In particular, indwelling catheters in the bladder cause, as foreign matter, inflammation of the urinary tract and/or the mucous membrane of the bladder and, once bacterial invasion takes place, the urine retained in the bladder serves as an excellent medium for bacterial growth and immediate infection will result.

A conventional measure prevailingly taken to cope with the above problem is chemotherapy using antibiotics. In that case, although the bacteria causative of the urinary tract infection may disappear, often thereafter bacterial strains resistant to the antibiotic administered appear newly. Therefore, chemotherapy undertaken without consideration of all possibilities might be rather dangerous because of the possibility of microbial substitution and infection by resistant strains as a result of the chemotherapy. The consensus today is that chemotherapy should be restricted to those cases alone where it is indispensable, such as cases of pyrexia due to pyelonephritis.

Under the above circumstances, techniques of releasing an antimicrobial agent locally at the application site of an indwelling urethral catheter have already been proposed. For instance, U.S. Pat. Nos. 3,566,874 and 3,695,921 disclose a process comprising providing a hydrophilic coated layer on the surface of a catheter by impregnating a catheter with a hydrophilic acrylate or methacrylate monomer or oligomer and carrying out the polymerization, and then impregnating the coated layer thus obtained, for example, with a quaternary ammonium salt compound, a type of cationic antimicrobial agent. However, catheters of this type are generally disadvantageous, among others, because (1) they are expensive since complicated after-treatment steps are required, (2) the antimicrobial activity is not long lasting because of an early exhaustion of the antimicrobial gent due to its premature migration into and diffusion in urine and other body fluids, and (3) once the salt concentration in the hydrophilic coated layer has reached a state of saturation as a result of absorption of urine and other body fluids, nuclei easily form there and calcium salts and other solid precipitates adhere thereto, possibly followed by catheter occlusion or difficulties in catheter extraction.

Further, Blandy, Brit. J. Hosp. Med., 4 (2), 179 (1970), discloses that urethral catheters should be washed with a 0.02% aqueous solution of Hibitane ® [product of ICI; generic name: chlorhexidine; chemical name: 1,6-di(4-chlorophenyldiguanido)hexane], a type of cationic antimicrobial agent, or reservoirs should be primed with Hibitane ®. A lubricant for urethral catheters which contains 0.02% Hibitane ® and lignocaine hydrochloride is also widely known. However, these are also basically disadvantageous in that the antimicrobial activity of the antimicrobial agent does not last long because of its premature migration into and diffusion in urine or other body fluids.

Today, in the fields of medical treatment, diagnosis, inspection, sanitation and food technology, a variety of microbicidal disinfectants are used for the prevention of contamination by bacteria and fungi of various kinds. Among them, cationic antimicrobial agents, which have potent microbicidal activity against a broad spectrum of microorganisms and low toxicity to the human body, constitute one of the classes most widely used among a large number of currently available microbicidal disinfectants.

However, so far there has not been any suggestion to incorporate these cationic antimicrobial agents into natural rubber latices, which have been widely used for a long time in the manufacture of products for medical and other uses because of their good moldability and processability and good physical characteristics of shaped articles made therefrom, followed by molding can give shaped natural rubber products capable of slowly releasing the cationic antimicrobial agents therefrom and forming a microbial growth inhibition zone therearound. This appears in fact an unexpected situation in view of the urgent need of avoiding microbial contamination encountered with urethral catheters, among others. One important reason is presumably that admixture of the above-mentioned cationic antimicrobial agents with the conventional natural rubber latices either causes instantaneous gelation (aggregation) of the natural rubber latices or results only in latex compositions having an unduly short pot life making molding difficult, so that the antimicrobial agents cannot be put into practical use. Specifically, although they have good moldability and processability and provide shaped goods with good physical properties, natural rubber latices have inferior chemical stability to synthetic polymer latices, and this fact has so far made it impossible to solve the above problem.

Generally, neutral rubber latex is a milk white sap exuded from a rubber tree when the latter is cut. From a compositional standpoint, it contains, as solids other than 35 to 40% by weight of rubbery hydrocarbons, about 2% by weight of proteins and small amounts (less than 1% by weight each) of fatty acids or esters thereof, sterols, complex lipids, sugars, inorganic matter, enzymes and so on. Natural rubber latices before compounding which are currently in use mostly contain 0.1 to 1% by weight of ammonia as a preservative for the prevention of bacterial growth in the latices, so that they are maintained at a pH of at least 9, generally 10 or higher, namely in the alkaline region. Compound latices used in molding various shaped products are compositions prepared by adding, as necessary, appropriate amounts of vulcanizing agent, vulcanization accelerator, filler, softening agent, antioxidant, dispersing agent, pH modifier, and other additives to the above latices. Even after compounding, the latex compositions are alkaline. As mentioned hereinbefore, addition of the above-mentioned cationic antimicrobial agents to such alkaline starting natural rubber latices or compound latices induces aggretation sooner or later depending on the quantity and the water solubility of these agents.

As regards the synthetic polymer latices, addition of an anionic surfactant and/or a nonionic surfactant before or after polymerization is common in the art, so that addition of cationic antimicrobial agents to these latices sooner or later also results in aggregation.

SUMMARY OF THE INVENTION

Intensive research has been conducted in order to provide antimicrobial latex compositions suitable for use in the manufacture of medical devices and appliances, sanitary products, equipment and furnishings for use in food manufacture and processing, and so forth, in particular antimicrobial latex compositions retaining good stability over a long period of storage. As a result, surprisingly, it was found that the desired end can be attained by incorporating the above-mentioned cationic antimicrobial agents into a cationic natural rubber latex or a cationic synthetic polymer latex. This finding has led to the present invention.

Thus, the invention provides an antimicrobial latex composition which comprises (1) at least one component selected from a cationic natural rubber latex and a cationic synthetic polymer latex and (2) a cationic antimicrobial agent incorporated in the latex.

It has also been found for the first time that stable natural rubber or synthetic polymer latex compositions with a cationic antimicrobial agent incorporated therein which have sufficiently long pot life to enable molding of various products including, among others, medical devices and appliances, can be produced. The above-mentioned cationic antimicrobial agent is released in a controlled manner continuously and persistently from the moldings produced from the compositions. When the molding is a urethral catheter, the antimicrobial agent is released in a controlled manner at a constant rate from the inside and outside surfaces of the indwelling catheter in use over a long period of time, so that an antimicrobial protective zone is formed on or around the surfaces and can contribute to a radical inhibition of urinary tract infection resulting from the invasion of bacteria from the outside The antimicrobial latex compositions of the present invention are also useful in manufacturing other articles which require long-period prevention against contamination by bacteria or fungi, such as diagnostic or inspection apparatus and devices, sanitary products, and equipment and furnishings for use in food manufacture and processing. For instance, they are useful in the manufacture of gloves (e.g., surgical gloves, gloves for use in food manufacture and processing, gloves for use in fishery), tubes, finger sacs, sponges, matresses, bathroom mats, rubber cloth products (e.g., aprons, bed sheets, diaper covers), binders for paper or nonwoven fabrics, rubber soles of footwear, slippers, ice bags, and so forth.

DETAILED DESCRIPTION OF THE INVENTION

The generic term "cationic antimicrobial agent" as used herein includes those antimicrobial agents which carry a positive charge per molecule or a basic group protonizable at a high rate in the physiological pH region and mostly have a hydrophobic group at the same time. Preferred cationic antimicrobial agents for use in the practice of the invention are biguanide compounds or salts thereof, acridine compounds or salts thereof, and quaternary ammonium salt compounds, among others. These antimicrobial agents are eventually incorporated in the matrix of the natural rubber or synthetic polymer moldings in a manner such that controlled release of the agents is possible. The agents are used in an amount selected depending on the respective purpose of use within the range of 0.01 to 50% by weight, preferably 0.01 to 40% by weight, more preferably 0.05 to 30% by weight, most preferably 0.1 to 10% by weight, based on a latex solids basis, such that they do not induce any serious deterioration in the physical properties of the moldings and no sign of toxicity in humans is observed.

These cationic antimicrobial agents may differ greatly in water solubility from readily soluble agents to sparingly soluble agents depending on the chemical structure of the basic skeleton thereof and the kind of salt. While all of them can effectively be used in practicing the invention, sparingly water-soluble ones are desirable for the manufacture of shaped products from which they should be released controlledly at a constant slow rate over a long period of time. It has actually been found that the use of such sparingly water-soluble antimicrobial agents can realize a surprising zero-order release during the period of actual use as a medical device, for instance. Such zero-order release is exceptional among matrix devices. The term "sparingly soluble" as used herein means that the solubility in 100 g of distilled water at 20° C. is in the range of 0.001 to 3 g, preferably 0.01 to 2 g.

Examples of biguanide compounds include compounds of the general formula (I), (II) or (III) given below.

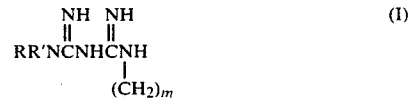 (I)

 (II)

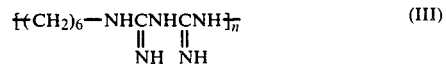 (III)

In the above formulae, R is an alkyl group, an aminoalkyl group, a phenyl group, an alkylphenyl group, a halophenyl group, a hydroxyphenyl group, a methoxyphenyl group, a carboxyphenyl group, a naphthyl group or a nitrile group; R' is a hydrogen atom or an alkyl group; and m and n each is a positive integer, preferably an integer within the range of 2 to 10. Typical preferred examples of suitable biguanide compounds are 1,6- di (4-chlorophenylbiguanido)hexane, diaminohexylbiguanide, 1,6-di(aminohexylbiguanido)hexane and polyhexamethylenebiguanide. biguanide.

Exemplary acridine compounds are compounds having the acridine skeleton (IV) shown below.

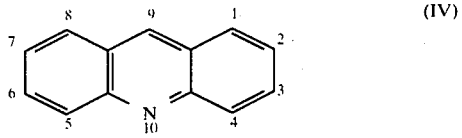

Various derivatives are described in *Dai Yuki Kagaku* (*Comprehensive Organic Chemistry*), Volume 16, pages 286 to 326 (Asakura Shoten, 1959). Preferred examples of suitable acridine compounds are 9-aminoacridine, 3,6-diaminoacridine and 6,9-diamino-2-ethoxyacridine.

The salts of biguanide or acridine compounds are salts formed with inorganic or organic acids, such as gluconic acid, lactic acid, hydrochloric acid, hydrobromic acid, nitric acid, sulfuric acid, carbonic acid, bicarbonic acid, citric acid, phosphoric acid, boric acid, formic acid, acetic acid, benzoic acid and tartaric acid.

Suitable quaternary ammonium salt compounds are represented by the structural formula (V) given below.

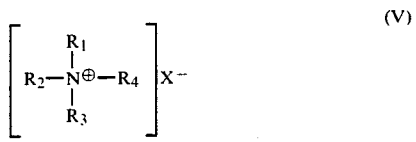

In formula (V), $R_1$, $R_2$, $R_3$ and $R_4$ each is an alkyl group, a benzyl group, a carboxyalkyl group, an alkyl-, nitro- or chloro-substituted benzyl group, a hydroxyalkyl group, an acetoxyalkyl group, an alkylphenoxyalkoxyalkyl group, or the like. A number of quaternary ammonium salt compounds with diverse $R_1$, $R_2$, $R_3$ and $R_4$ groups combined therein are described in *Encyclopedia of Chemical Technology*, Volume 19, pages 521–531 (*Wiley International Publication*, 1982), *Kaimen Kasseizai Binran* (*Manual of Surfactants*), edited by Nishi, Imai and Kasai, pages 737 to 747 (Sangyo Tosho, 1960), and R.S. Shelton et al., *Journal of the American Chemical Society*, Volume 68, pages 753–759 (1946). In the practice of the invention, benzyldimethyldodecylammonium salts in which $R_1$ is benzyl, $R_2$ and $R_3$ are each methyl and $R_4$ is dodecyl, benzyldimethyltetradecylammonium salts in which $R_1$ is benzyl, $R_2$ and $R_3$ are each methyl and $R_4$ is tetradecyl, benzyldimethylhexadecylammonium salts in which $R_1$ is benzyl, $R_2$ and $R_3$ are each methyl and $R_4$ is hexadecyl, trimethyltetradecylammonium salts in which $R_1$, $R_2$ and $R_3$ are each methyl and $R_4$ is tetradecyl, and benzethonium salts in which $R_1$ is benzyl, $R_2$ and $R_3$ are each methyl and $R_4$ is {2-[2-p-(1,1,3,3-tetramethylbutyl)phenoxy]ethoxy}ethyl, among others, are preferably used. Generally, X is chloride, bromide, iodide, citrate, sulfate, phosphate, borate or the like. Those polymer type quaternary ammonium salt compounds in which one of $R_1$, $R_2$, $R_3$ and $R_4$ is the principal polymer chain and the quaternary ammonium slat moiety is chemically incorporated as the side chain are also effective in the practice of this invention.

Examples of the sparingly water-soluble antimicrobial agents which are particularly preferred among the cationic antimicrobial agents which can be used in the practice of this invention include the hydrochloride, acetate or sulfate of 1,6-di(4-chlorophenylbiguanido)hexane, the lactate or hydrochloride of 6,9-diamino-2ethoxyacridine, the sulfate of 3,6-diaminoacridine, benzyldimethyltetradecylammonium iodide, benzyldimethylhexadecylammonium phosphate and benzethonium iodide, among others.

The term "cationic natural rubber latex" as used herein means the so-called acidic latex, also called positex, which has a pH not greater than about 4.7, which is the isoelectric point of proteins serving as dispersion stabilizers in the natural rubber latex, preferably a pH not greater than 3. In that state, rubber particles carry a positive charge which is contrary to that in usual alkaline natural rubber latices.

A cationic natural rubber can be prepared by adding, to a usual natural rubber latex (50 to 60 wt% solids, pH 9 to 11), a cationic surfactant and/or a nonionic surfactant in an amount of 0.1 to 20% by weight, preferably 1 to 5% by weight, based on the rubber solids, followed by adjustment of the pH to not more than about 4.7, preferably not more than 3, with an appropriate inorganic acid such as hydrochloric acid, etc., or organic acid such as gluconic acid, etc.

The synthetic polymer latices usable in the practice of the invention include, among others, those containing, as the main component, at least one member selected from the group consisting of silicones; polyurethanes; homopolymers and copolymers of vinyl monomers such as ethylene, styrene, vinyl acetate, vinyl chloride, vinylidene chloride, tetrafluoroethylene, trifluoroethylene, acrylonitrile, (meth)acrylate esters, vinylpyridine and methyl vinyl ether; homopolymers and copolymers of diene monomers such as butadiene, isoprene, 1,3-pentadiene, 1,5-hexadiene, 1,6-heptadiene and chloroprene; copolymers of vinyl monomers such as those mentioned above and diene monomers such as those mentioned above; copolymers of vinyl monomers containing, as a functional group, an epoxy, amino, carboxyl, acid anhydride, hydroxyl, amido, N-methylolamido or isocyanato group and any of the monomers mentioned above; with a surfactant, a catalyst, a cross-linking agent, a crosslinking promoter, a filler, a stabilizer and other additives added as necessary. The term "cationic synthetic latex" as used herein refers to a latex which also contains a cationic surfactant and/or a nonionic surfactant and in which the latex particles substantially carry a positive electric charge.

The cationic surfactant preferably used in the natural rubber or synthetic polymer latices in accordance with this invention includes, among others, alkylpyridinium salts, higher aliphatic monoamine or diamine salts and quaternary ammonium salts. The nonionic surfactant to be used includes, among others, polyoxyethylene alkyl ethers, polyoxyethylene alkylphenol ethers, polyoxyethylene fatty acid esters, sorbitan fatty acid esters and polyoxyethylenesorbitan fatty acid esters. These cationic surfactants and nonionic surfactants are used either alone or in combination depending on the purpose of use, generally in an amount of about 0.1 to 20% by weight, preferably 1 to 5% by weight, on a latex solids basis. Although the latex compositions according to this invention may slightly contain an anionic surfactant as a dispersion stabilizer for various additives used, the content of such anionic surfactant should be kept at a level not exceeding the positive electric charges of the above-mentioned cationic surfactant and/or nonionic surfactant, preferably a level not exceeding one-half, more preferably a level not exceeding one tenth of the content of the positive electric charges.

The antimicrobial latex compositions according to this invention can be prepared using any of the various known methods of blending components to produce a homogeneous mixture. With a readily water-soluble antimicrobial agent, for instance, the agent may be added in the form of a solution directly to the latices. On the other hand, a sparingly water-soluble antimicrobial agent preferably is milled in a ball mill or the like together with an appropriate dispersing agent and then added, in the form of a homogeneous paste-like dispersion in water, to the latices.

Among the compositions according to the invention, those comprising a cationic antimicrobial agent and a natural rubber latex are very useful in manufacturing medical devices and appliances, such as urethral catheters, since those products made therefrom have the ability to release the antimicrobial agent slowly and persistently over a long period of time. Preferred urethral catheters are those which have a layer made from the composition according to this invention on the inside surface and/or outside surface thereof since this design for the catheters, when used in patients, produces a microbial growth inhibiting zone around the same to thereby prevent urinary tract infection from the outside. It is also preferable to provide, on the surface of the urethral catheters having the above antimicrobial agents, a drug-free coated layer of a natural rubber (homologous polymer) or a silicone rubber (heterologous polymer) to thereby adjust the rate of controlled release of the antimicrobial agent depending on the intended use of the catheters or decrease possible irritancy thereof to the surface contacting the body. In particular, a silicone rubber coating on the inside and outside surfaces of urethral catheters made of natural rubber is preferred since the rate of release of the antimicrobial agent is controlled. Further the irritation to the urethral mucosa is diminished and the adhesion of calcium salts in urine and body fluids is prevented. To produce such coating, an antimicrobial agent-free or antimicrobial agent-containing silicone latex is preferably used.

The present invention also provides a method of manufacturing shaped articles capable of releasing a cationic antimicrobial agent in a controlled manner by the dip forming using a dipping fluid comprising a cationic antimicrobial agent/latex composition, which method is characterized in that a latex which contains a cationic surfactant and/or nonionic surfactant and in which latex particles substantially carry a positive electric charge is used as the latex component in the dipping fluid composition. The dip forming referred to herein is a process comprising dipping a dipping former in a dipping fluid to thereby cause the dipping fluid components to precipitate on the surface of the dipping former and drying the precipitate, and repeating the dipping and drying steps one to a large number of times followed by removing the thus-shaped article from the dipping former. For instance, urethral catheters made of natural rubber are currently being manufactured by the continuous dip molding process. In that case, the latex is retained in the dipping vessel for several months while the daily decrement is compensated for in an appropriate manner. Therefore, the latter must have storage stability for a longer period of time. In this respect, the antimicrobial latex compositions according to the invention have a very long pot life and are accordingly particularly suited for that purpose. In accordance with this invention, the desired end can be attained very economically and efficiently using currently available apparatus and equipment without any particular after-treatment steps being required.

It goes without saying that the antimicrobial latex compositions according to the invention can also be used in other molding processes which do not require such a long pot life as the above dip forming requires, for example, in casting, extrusion, foam rubber manufacture, fiber surface treatment and fiber bonding processes. In the preparation of the antimicrobial latex compositions according to this invention, it is of course possible to use not only one single latex component but also two or more latex components in admixture.

The following examples are given to further illustrate the present invention. However, the scope of the invention is not limited to these examples. In the examples, "part(s)" means "part(s) by weight".

EXAMPLE 1

A mixture of 0.5 part of sulfur, 0.7 part of zinc dibutyldithiocarbamate, 0.3 part of zinc white, 0.1 part of sodium alkylsulfonate and 5 parts of water was milled well in a ball mill for about 50 hours to obtain a paste-like mixture. This mixture was added to 100 parts of a nautral rubber latex solution (pH 10.7) with a solids content of about 50% to produce a compound latex (Composition A) containing natural rubber as the main component.

Then, 2 parts of polyoxyethylene nonylphenyl ether (the number of EtO groups is 10), a nonionic surfactant, was added to Composition A, followed by adjustment of the pH to 3.0 by dropwise addition of a 5 N aqueous solution of hydrochloric acid. To the thus-prepared cationic natural rubber latex (Composition B), there was added 15 parts of a 20% (w/v) solution of 1,6-di(4-chlorophenylbiguanido)hexane gluconate, a readily water-soluble cationic antimicrobial agent, in water, followed by stirring. The resultant mixture was stable for more than 3 months without showing any sign of gelation.

COMPARATIVE EXAMPLE 1

To Composition A prepared as described in Example 1, there was added 5 parts of a 20% (w/v) aqueous solution of 1,6-di(4-chlorophenylbiguanido)hexane gluconate, followed by stirring. Gelation occurred immediately.

EXAMPLE 2

To Composition B prepared as described in Example 1, there was added 5 parts of powdery 1,6-di(4-chlorophenylbiguanido)hexane hydrochloride, a sparingly water-soluble, cationic antimicrobial agent, followed by stirring. The resultant mixture was stable for more than 3 months without showing any sign of gelation.

COMPARATIVE EXAMPLE 2

To Composition A prepared as described in Example 1, there was added 1 part of powdery 1,6-di(4-chlorophenylbiguanido)hexane hydrochloride, the same antimicrobial agent as used in Example 2, followed by stirring. The mixture gelled on the next day.

EXAMPLE 3 AND COMPARATIVE EXAMPLE 3

To Composition A prepared as described in Example 1, there was added 1 part of sparingly water-soluble 6,9-diamino-2-ethoxyacridine lactate. The resultant mixture gelled on the next day. On the other hand, a mixture prepared by adding the above antimicrobial agent to Composition B prepared as described in Example 1 remained stable for more than 3 months without showing any sign of gelation.

EXAMPLE 4 AND COMPARATIVE EXAMPLE 4

To Composition A prepared as described in Example 1, there was added 5 parts of a 10% (w/v) aqueous solution of readily water-soluble lauryldimethylbenzylammonium chloride, whereupon gelation occurred. On the other hand, when the above antimicrobial agent was added to Composition B prepared as described in Example 1, the resultant mixture remained stable for more than 3 months without showing any sign of gelation.

EXAMPLE 5

The cationic natural rubber latex composition containing 1,6-di(4-chlorophenylbiguanido)hexane gluconate prepared as described in Example 1 was molded by casting, drying at room temperature for 24 hours and heating at 80° C. for 24 hours to produce a vulcanized natural rubber sheet having a size of 60 mm×100 mm×1 mm in thickness.

The natural rubber sheet thus obtained was immersed in 100 ml of water at 37° C. for 1 day for testing. The water was then tested for antimicrobial activity by the cylinder plate method using *Bacillus subtilis* ATCC 6633 as the test organism (medium: nutrient agar). Formation of a circular inhibition zone indicative of the inhibition of bacterial growth was noted and it was thus confirmed that the above antimicrobial agent was present in the water. The same antimicrobial activity test was repeated while replacing the water for testing with a fresh portion of water every day. The inhibition zone formation was observed until the 62nd day.

COMPARATIVE EXAMPLE 5

A natural rubber sheet having the same shape and size and prepared in the same manner as that described in Example 5 except that it contained no antimicrobial agent was immersed in a 20% (w/v) aqueous solution of 1,6-di(4-chlorophenylbiguanido)hexane gluconate at room temperature for 2 weeks and then dried. The resultant sheet was subjected to the same antimicrobial activity testing as described in Example 5. On the first day of testing, a circular inhibition zone was formed but thereafter no inhibition zone was observed at all.

EXAMPLE 6

Using the cationic natural rubber latex composition prepared as described in Example 2 and containing 1,6-di(4-chlorophenylbiguanido)hexane hydrochloride, the procedures of Example 5 were followed to produce a similar natural rubber sheet. The sheet was subjected to antimicrobial activity testing. The antimicrobial agent concentration in the water for testing was followed at timed intervals using the relationship between antimicrobial agent concentration and inhibition zone size as indicated by a working curve constructed beforehand. Controlled release at a constant rate which could be considered to be substantially of the zero order was noted for a little more than one month. Ultimately, inhibitory zone formation was observed until the 122nd day.

EXAMPLE 7

In an existing line for the continuous production of urethral catheters by the dip forming, urethral catheters were manufactured in the conventional manner except that a cationic natural rubber latex composition containing 1,6-di(4-chlorophenylbiguanido)hexane hydrochloride in an amount of 20% by weight (for first dipping) or 1% by weight (for last dipping) based on the rubber solid content was used as the dipping fluid in the first dipping step and the final (9th) dipping step. The line was operated continuously for 3 months while making up for the daily decrement of the dipping fluid (about 10% by volume) in the dipping vessel in an appropriate manner. The operation could be conducted smoothly without any difficulties such as viscosity increase or aggregation.

In this manner, urethral catheters containing 20% by weight of the antimicrobial agent in the inside surface layer and 1% by weight of the same agent in the outside surface layer and capable of controlled release of the agent were manufactured. Using these urethral catheters, a clinical test was performed in 5 patients. For the 2 weeks when the catheter was in the bladder, no urinary tract infection was observed in any of the cases.

COMPARATIVE EXAMPLE 6

Using antimicrobial agent-free conventional urethral catheters, a clinical test was performed in 5 patients in the same manner as described for Example 7. Urinary tract infection was observed on the third day in 2 of the patients, on the 4th day in another patient and on the 5th day in a further patient.

EXAMPLE 8 AND COMPARATIVE EXAMPLE 7

To 100 parts of an anionic silicone latex with a solids content of about 30% by weight, there was added 2 parts of 1,6-di(4-chlorophenylbiguanido)hexane gluconate. Several hours later, a precipitate formed. On the other hand, when the same antimicrobial agent was added to a cationic silicone latex having a solids content of about 30% by weight, the resulting mixture remained stable for more than 3 months without any precipitate formation.

EXAMPLE 9 AND COMPARATIVE EXAMPLE 8

To 100 parts of an anionic chloroprene latex with a solids content of about 40% by weight, there was added 10 parts of a 10% (w/v) aqueous solution of trimethyltetradecylammonium bromide, whereupon a precipitate formed. When the same aqueous antimicrobial agent solution was added to a cationic chloroprene latex having a solids content of about 35% by weight, the resulting mixture remained stable for more than 3 months.

EXAMPLE 10

To a mixture of 100 parts of cationic natural rubber latex Composition B prepared as described in Example 1 and 30 parts of a cationic butadiene-styrene copolymer latex with a solids content of about 35% by weight, there was added 5 parts of 1,6-di(4-chlorophenylbiguanido) hexane acetate. The mixture thus obtained remained stable for more than 3 months without showing any sign of gelation.

While the invention has been described in detail and with reference to specific embodiments thereof, it will be apparent to one skilled in the art that various changes and modifications can be made therein without departing from the spirit and scope thereof.

What is claimed is:

1. An antimicrobial latex composition which comprises (1) at least one cationic latex component selected from a cationic natural rubber latex and a cationic synthetic polymer latex and (2) a cationic antimicrobial agent incorporated in said cationic latex (1).

2. The composition of Claim 1, wherein the cationic antimicrobial agent (2) is a biguanide compound or a salt thereof.

3. The composition of Claim 2, wherein the biguanide compound is selected from the group consisting of 1,6-di(4-chlorophenylbiguanido)hexane, diaminohexylbiguanide, 1,6-di(aminohexylbiguanido)hexane and polyhexamethylenebiguanide.

4. The composition of Claim 1, wherein the cationic antimicrobial agent (2) is an acridine compound or a salt thereof.

5. The composition of Claim 4, wherein the acridine compound is selected from the group consisting of 9-aminoacridine, 3,6-diaminoacridine and 6,9-diamino-2-ethoxyacridine.

6. The composition of Claim 1, wherein the cationic antimicrobial agent (2) is a quaternary ammonium salt compound.

7. The composition of Claim 6, wherein the quaternary ammonium salt compound is selected from the group consisting of a benzyldimethyldodecylammonium salt, a benzyldimethyltetradecylammonium salt, a benzyldimethylhexadecylammonium salt, a trimethyltetradecylammonium salt and a benzethonium salt.

8. The composition of Claim 1, wherein the cationic antimicrobial agent (2) is a sparingly water-soluble cationic antimicrobial agent.

9. The composition of Claim 8, wherein the sparingly water-soluble cationic antimicrobial agent is selected from the group consisting of the hydrochloride, acetate or sulfate of 1,6-di(4-chlorophenylbiguanido)hexane, the lactate or hydrochloride of 6,9-diamino-2ethoxyacridine, 3,6-diaminoacridine sulfate, benzyldimethyltetradecylammonium iodide, benzyldimethylhexadecylammonium phosphate and benzethonium iodide.

10. The composition of Claim 1, wherein the amount of the cationic antimicrobial agent (2) present is about -0.01 to about 50% by weight based on the latex solids content of the latex (1).

11. A shaped article produced from the antimicrobial latex composition of Claim 1.

12. The shaped article of Claim 11, in the form of a urethral catheter.

13. A method of manufacturing a shaped article comprising dipping a dipping former in a dipping fluid containing a cationic natural rubber or synthetic polymer latex and a cationic antimicrobial agent to thereby cause the dipping fluid components to precipitate on the surface of the dipping former and drying the precipitate and repeating the dipping and drying steps one to a large number of times followed by removing the thus-shaped article from the dipping former.

14. The method of Claim 13, wherein the shaped article is a urethral catheter.

* * * * *